(12) United States Patent
Blackbourn et al.

(10) Patent No.: US 9,873,665 B2
(45) Date of Patent: Jan. 23, 2018

(54) PROCESS FOR TREATING BIOMASS TO PRODUCE MATERIALS USEFUL FOR BIOFUELS

(71) Applicant: SHELL OIL COMPANY, Houston, TX (US)

(72) Inventors: Robert Lawrence Blackbourn, Houston, TX (US); Paul Richard Weider, Houston, TX (US); Dennis Shane Boriski, Houston, TX (US)

(*) Notice: Subject to any disclaimer, the term of this patent is extended or adjusted under 35 U.S.C. 154(b) by 79 days.

(21) Appl. No.: 14/825,337

(22) Filed: Aug. 13, 2015

(65) Prior Publication Data

US 2016/0046567 A1    Feb. 18, 2016

Related U.S. Application Data

(60) Provisional application No. 62/037,198, filed on Aug. 14, 2014.

(51) Int. Cl.
| | |
|---|---|
| *C13K 1/02* | (2006.01) |
| *C12P 7/10* | (2006.01) |
| *C07C 309/08* | (2006.01) |
| *C13K 13/00* | (2006.01) |
| *D21C 1/04* | (2006.01) |
| *D21C 3/04* | (2006.01) |

(52) U.S. Cl.
CPC .......... *C07C 309/08* (2013.01); *C13K 1/02* (2013.01); *C13K 13/00* (2013.01); *C13K 13/002* (2013.01); *D21C 1/04* (2013.01); *D21C 3/04* (2013.01); *C12P 2201/00* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 3,549,319 | A | 12/1970 | Wilson et al. |
| 4,409,032 | A | 10/1983 | Paszner et al. |
| 4,461,648 | A | 7/1984 | Foody |
| 5,536,325 | A | 7/1996 | Brink |
| 5,789,210 | A | 8/1998 | Ho et al. |
| 6,475,768 | B1 | 11/2002 | Otero et al. |
| 7,741,084 | B2 | 6/2010 | Viitanen et al. |
| 7,741,119 | B2 | 6/2010 | Viitanen et al. |
| 7,781,191 | B2 | 8/2010 | Dunson, Jr. et al. |
| 2003/0162271 | A1 | 8/2003 | Zhang et al. |
| 2008/0216391 | A1 | 9/2008 | Cortright et al. |
| 2009/0061490 | A1 | 3/2009 | Edwards et al. |
| 2011/0154721 | A1 | 6/2011 | Chheda et al. |
| 2011/0282115 | A1 | 11/2011 | Chheda et al. |
| 2012/0122152 | A1 | 5/2012 | Blackbourn et al. |
| 2013/0196400 | A1 | 8/2013 | Weider et al. |
| 2013/0295629 | A1 | 11/2013 | Weider et al. |

FOREIGN PATENT DOCUMENTS

| | | |
|---|---|---|
| EP | 1727890 | 12/2006 |
| WO | 9513362 | 5/1995 |
| WO | 9742307 | 11/1997 |
| WO | 2006096130 | 9/2006 |
| WO | 2007028811 | 3/2007 |
| WO | 2007136762 | 11/2007 |
| WO | 2008119082 | 10/2008 |
| WO | 2007009463 | 11/2008 |
| WO | 2009109631 | 9/2009 |
| WO | 2012061596 | 5/2012 |
| WO | 2013169706 | 11/2013 |

OTHER PUBLICATIONS

International Search Report dated Nov. 9, 2015 of PCT/US2015/045014 filed Aug. 13, 2015.
Mosier, C.W. et al.; :Features of promising technologies for pre-treatment of lignocellulosic biomass; Bioresource Technology; vol. 96; pp. 673-686; 2005.
Holtzapple, M. T., et al.; "The ammonia freeze explosion (AFEX) process—a practical lignocellulose pretreatment"; Applied Biochemistry and Biotechnology; vols. 28/29; pp. 59-74; 1991.
Kumar, P. et al.; "Methods for Pretreatment of Lignocellulosic Biomass for Efficient Hydrolysis and Biofuel Production"; Ind. Eng. Chem. Res., vol. 48, No. 8; pp. 3713-3729; 2009.
Lavarack, G. J. et al.; "The acid hydrolysis of sugarcane bagasse hemicelluloses to product xylose, arabinose, glucose and other products"; Biomass and Bioenergy; vol. 23; pp. 367-380; 2002.
Brown C. et al.; "Fast Pyrolysis and Bio-oil Upgrading, Biomass-to-Diesel Workshop", Pacific Northwest National Laboratory, Richland, Washington, Sep. 5-6, 2006; 46 pages.

*Primary Examiner* — Karen Cochrane Carlson
*Assistant Examiner* — Jennifer M. H. Tichy (57) ABSTRACT

Since biomass is always accompanied by caustic inorganic materials, we have found that the formation of the anion salt of α-hydroxysulfonic acid represent the largest "loss" of the α-hydroxysulfonic acid in the potential reversible acid pre-treatment process. By titrating the α-hydroxysulfonic acid salt with strong mineral acid and then reverting the alfa-hydroxysulfonic acid as its primary components, the acid components can be recovered substantially quantitatively.

32 Claims, 5 Drawing Sheets

PROCESS FOR TREATING BIOMASS TO PRODUCE MATERIALS USEFUL FOR BIOFUELS

This application claims the benefit of U.S. Provisional Application No. 62/037,198, filed on Aug. 14, 2014, which is incorporated herein by reference.

FIELD OF THE INVENTION

The invention relates to a process for treating biomass, and more specifically to a pretreatment of biomass for the production of sugars from materials containing polysaccharides and compositions, for use in biofuel or other high value products.

BACKGROUND OF THE INVENTION

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. These structural components are comprised primarily of pentose and hexose sugars monomers. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. In order to overcome recalcitrance ground biomass is altered by a chemical process known as pretreatment. The aim of the pretreatment is to hydrolyze the hemicellulose, break down the protective lignin structure and disrupt the crystalline structure of cellulose. All of these steps enhance enzymatic accessibility to the cellulose during the subsequent hydrolysis (saccharification) step.

Pretreatment is viewed as one of the primary cost drivers in lignocellulosic ethanol and as a consequence a number of pretreatment approaches have been investigated on a wide variety of feedstocks types. The Saccharification of the cellulose enzymatically holds promise of greater yields of sugars under milder conditions and is therefore considered by many to be more economically attractive. The recalcitrance of the raw biomass to enzymatic hydrolysis necessitates a pretreatment to enhance the susceptibility of the cellulose to hydrolytic enzymes. A number of pretreatment methods, such as described in Nathan Mosier, Charles Wyman, Bruce Dale, Richard Elander, Y. Y. Lee, Mark Holtzapple, Michael Ladisch *'Features of promising technologies for pretreatment of lignocellulosic biomass"* Bioresource Technology 96 (2005) pp. 673-686, have been developed to alter the structural and chemical composition of biomass to improve enzymatic conversion. A very recent comparison of "leading pretreatment" technologies was accomplished by the Biomass Refining Consortium for Applied Fundamentals and Innovation (CAFI) and reported out in the journal *Bioresource Technology* in December of 2011. Such methods include treatment with dilute acid steam explosion described in U.S. Pat. No. 4,461,648, hydrothermal pretreatment without the addition of chemicals described in WO 2007/009463 A2, ammonia freeze explosion described in AFEX; Holtzapple, M. T., Jun, J., Ashok, G., Patibandla, S. L., Dale, B. E., 1991, *The ammonia freeze explosion (AFEX) process—a practical lignocellulose pretreatment*, Applied Biochemistry and Biotechnology 28/29, pp. 59-74, and organosolve extraction described in U.S. Pat. No. 4,409,032. Despite this, pretreatment has been cited as the most expensive process in biomass-to-fuels conversion ("Methods for Pretreatment of Lignocellulosic Biomass for Efficient Hydrolysis and Biofuel Production" Ind. Eng. Chem. Res., 2009, 48(8), 3713-3729.)

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that enzymatic Saccharification is successful. The parameters which can be employed to control the conditions and effectiveness of the pretreatment are time, temperature, and acid loading. These are often combined in a mathematical equation termed the combined severity factor. In general, the higher the acid loading employed, the lower the temperature that can be employed; this comes at a cost of acid and its subsequent neutralization. Conversely, the lower the temperature, the longer the pretreatment process takes; this comes at the cost of volumetric productivity. It is desirable to lower the temperature because pentose sugars readily decompose to form furfurals and other species which represents a yield loss and these compounds are poisons to downstream fermentation. However the use of the higher concentrations of acid required to lower the pretreatment temperatures below that where furfural formation becomes facile (B. P. Lavarack, G. J. Griffin, D. Rodman "The acid hydrolysis of sugarcane bagasse hemicelluloses to product xylose, arabinose, glucose and other products." *Biomass and Bioenergy* 23 (2002) pp. 367-380) requires sufficient quantities of acid that the recovery of the strong acid is an economic imperative. If dilute acid streams and higher temperatures are employed the pretreatment reaction produces increased amounts of furfural and the acid passing downstream must be neutralized resulting in inorganic salts which complicates downstream processing and requires more expensive waste water treatment systems.

More recently, in US20120122152, α-hydroxysulfonic acids have been shown to be effective in the pretreatment and hydrolysis of biomass with the additional benefit of being recoverable and recyclable through reversal to the acids primary components (aldehyde, $SO_2$ and water). This pretreatment process has been shown to provide numerous benefits compared to dilute mineral acid pretreatment.

SUMMARY OF THE INVENTION

When α-hydroxysulfonic acid encounters a basic species, such as a carbonate, the anionic salt form of the acid is generated. This acid salt is not reversible as the α-hydroxysulfonic acid must be in the protonic form to revert to primary components. Since biomass is always accompanied by caustic inorganic materials, we have found that the formation of the anion salt of α-hydroxysulfonic acid represent the largest "loss" of the α-hydroxysulfonic acid in the potential reversible acid pretreatment process.

We have found that by titrating the α-hydroxysulfonic acid salt with strong mineral acid and then reverting the alfa-hydroxysulfonic acid as its primary components, the acid components can be recovered. If the α-hydroxysulfonic acid cannot be recycled, it is expensive relative to mineral acids. Thus, by recovering the α-hydroxysulfonic acid from its acid salt, provides for a cost reduction in the treatment process.

In an embodiment of the present invention, a method for recovering α-hydroxysulfonic acid in a biomass treatment process comprising:

(a) providing a biomass containing polysaccharides;
(b) contacting the biomass with a solution containing at least one α-hydroxysulfonic acid thereby hydrolyzing the biomass to produce a product stream containing at least one fermentable sugar, α-hydroxysulfonic acid, and at least one salt of α-hydroxysulfonic acid;
(c) contacting at least a portion of the salt of α-hydroxysulfonic acid with a mineral acid forming α-hydroxysulfonic acid and a salt of the mineral acid;
(d) separating at least a portion of the α-hydroxysulfonic acid from the mineral acid by heating and/or reducing pressure and recovering the α-hydroxysulfonic acid in its component form; and
(e) recovering from the product stream an acid-removed product containing at least one fermentable sugar.

The α-hydroxysulfonic acid can be recovered by removing the α-hydroxysulfonic acid in its component form from the product by heating and/or reducing pressure to produce an acid-removed product containing at least one fermentable sugar substantially free of the α-hydroxysulfonic acid.

In an embodiment of the present invention, a method for recovering α-hydroxysulfonic acid in a biomass treatment process comprising:

(a) providing a biomass containing polysaccharides;
(b) contacting the biomass with a solution containing at least one α-hydroxysulfonic acid in an amount of from about 1% wt. to about 55% wt., based on the solution, at a temperature within the range of about 50° C. to about 150° C. and a pressure within the range of 0.5 bara to about 11 bara thereby hydrolyzing the biomass to produce a product stream containing at least one fermentable sugar, α-hydroxysulfonic acid, and at least one salt of α-hydroxysulfonic acid;
(c) contacting at least a portion of the salt of α-hydroxysulfonic acid with a mineral acid in an amount from about 0.1 equivalent to about 1.2 equivalent amount of mineral acid to the salt of α-hydroxysulfonic acid, said mineral acid is selected from the group consisting of sulfuric acid, phosphoric acid, hydrochloric acid, and mixtures thereof, at a temperature within the range from about 50° C. to about 150° C. forming α-hydroxysulfonic acid and a salt of the mineral acid;
(d) separating at least a portion of the α-hydroxysulfonic acid from the mineral acid at a temperature within the range from about 50° C. to about 150° C. and a pressure within the range from about 0.1 bara to about 5 bara with the proviso that (i) the temperature is higher than step (b), (ii) the pressure is less than step (b) or (iii) the temperature is higher and pressure is lower than step (b), and recovering the α-hydroxysulfonic acid in its component form; and
(e) recovering from the product stream an acid-removed product containing at least one fermentable sugar.

In an embodiment, an acid-removed product is further processed to produce at least one organic compound.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

DETAILED DESCRIPTION OF THE INVENTION

It has been found that the present invention provides an improved method for the acid treatment of biomass in a process for producing sugars and biofuels. If the α-hydroxysulfonic acid cannot be recycled, it is expensive relative to mineral acids. We have found that by titrating the α-hydroxysulfonic acid salt with strong mineral acid and then reverting the α-hydroxysulfonic acid as its primary components, the acid components can be recovered virtually quantitatively providing for a cost reduction in the reversible acid pretreatment process.

By adding about a molar equivalent amount of a mineral acid (e.g., hydrochloric, sulfuric or phosphoric acid) to a solution of salts of alfa-hydroxysulfonic acids, an equilibrium can be achieved between the protonic and mineral salt versions of the acids. As only the alfa-hydroxysulfonic acid is reversible to volatile components, following Le Chatelier's principle, all of the alpha-hydroxysulfonic acid can be recovered and the salt of the mineral acid is formed.

The α-hydroxysulfonic acid is effective for treatment of biomass hydrolyzing the biomass to fermentable sugars like pentose such as xylose at lower temperature, (e.g., about 100° C. for α-hydroxymethane sulfonic acid or α-hydroxyethane sulfonic acid) producing little furfural in the process. A portion of the cellulose has also been shown to hydrolyze under these comparatively mild conditions. Other polysaccharides such as starch are also readily hydrolyzed to component sugars by α-hydroxysulfonic acids. Further, the α-hydroxysulfonic acid is reversible to readily removable and recyclable materials unlike mineral acids such as sulfuric, phosphoric, or hydrochloric acid. The lower temperatures and pressures employed in the biomass treatment leads to lower equipment cost. The ability to recycle fragile pentose sugars from the end of pretreatment to the inlet of pretreatment, without their subsequent conversion to undesirable materials such as furfural, allows lower consistencies in the pretreatment reaction itself, yet still passing a high consistency solids mixture containing high soluble sugars out of pretreatment. Biomass pretreated in this manner has been shown to be highly susceptible to additional saccharification, especially enzyme mediated saccharification.

Using pretreatment at high temperatures and dilute acid, free xylose is readily dehydrated to form a toxic byproduct, furfural. Thus, in elevated temperature dilute acid processes it is desirable to terminate the pretreatment reaction as soon as the majority of the xylan has been hydrolyzed in order to minimize xylose decomposition. Any free sugars recycled into the front end of an elevated temperature pretreatment process would immediately decompose and result in very high levels of furfurals with no real increase of sugars. This would preclude any attempts at recycling pretreatment liquids to build soluble sugar levels. Thus, in higher temperature, once through pretreatments, the amount of acid solution to "dry weight" biomass introduced in pretreatment determines the ultimate concentration of fermentable sugar obtained. This is balanced by the absorptive nature of biomass with mixing, transport and heat transfer becoming increasingly difficult as the relative amount of biomass solids to liquid is increased. The process utilizes low severity conditions (e.g. low temperature) that are possible with pretreatment using higher concentrations of α-hydroxysulfonic acids, enabling the recycle and build up of sugars in the pre-treatment reactor stage. The lower temperature process dramatically reduces the rate of C5 and C6 sugar decomposition to other species such as furfural. Thus, free sugars can be introduced (via recycle) into the front end of a low temperature process and they will pass largely unchanged through pretreatment. This allows buildup of high concentrations of steady state sugars while handling lower consistency in the pretreatment process. The lower temperature has other advantages as if the temperatures are below the reported lignin melting point, the lignin in the biomass is largely unaltered in texture which results in a non-fouling free flowing pre-treated material. This enables a facile liquid/solid separation at the end of the pretreatment.

The α-hydroxysulfonic acids have the general formula wherein $R_1$ and $R_2$ are individually hydrogen or hydrocarbyl with up to about 9 carbon atoms that may or may not contain oxygen can be used in the treatment of the instant invention. The alpha-hydroxysulfonic acid can be a mixture of the aforementioned acids. The acid can generally be prepared by reacting at least one carbonyl compound or precursor of carbonyl compound (e.g., trioxane and paraformaldehyde) with sulfur dioxide or precursor of sulfur dioxide (e.g., sulfur and oxidant, or sulfur trioxide and reducing agent) and water according to the following general equation 1.

where $R_1$ and $R_2$ are individually hydrogen or hydrocarbyl with up to about 9 carbon atoms or a mixture thereof.

Illustrative examples of carbonyl compounds useful to prepare the alpha-hydroxysulfonic acids used in this invention are found where $R_1$=$R_2$=H (formaldehyde)
$R_1$=H, $R_2$=$CH_3$ (acetaldehyde)
$R_1$=H, $R_2$=$CH_2CH_3$ (propionaldehyde)
$R_1$=H, $R_2$=$CH_2CH_2CH_3$ (n-butyraldehyde) $R_1$=H, $R_2$=$CH(CH_3)_2$ (i-butyraldehyde)
$R_1$=H, $R_2$=$CH_2OH$ (glycolaldehyde)
$R_1$=H, $R_2$=$CHOHCH_2OH$ (glyceraldehdye)
R1=H, R2=C(=O)H (glyoxal)
$R_1$ = H, $R_2$ = CCHCHCHO (furfural)
$R_1$ = H, $R_2$ = C(CH)$_4$C(OH) (salicylaldehyde)
$R_1$ = H, $R_2$ = C(CH)$_4$CH (benzaldehyde)

$R_1$=$R_2$=$CH_3$ (acetone)
$R_1$=$CH_2OH$, $R_2$=$CH_3$ (acetol)
$R_1$=$CH_3$, $R_2$=$CH_2CH_3$ (methyl ethyl ketone)
$R_1$=$CH_3$, $R_2$=$CHC(CH_3)_2$ (mesityl oxide)
$R_1$=$CH_3$, $R_2$=$CH_2CH(CH_3)_2$ (methyl i-butyl ketone)
$R_1$, $R_2$=$(CH_2)_5$ (cyclohexanone) or
$R_1$=$CH_3$, $R_2$=$CH_2Cl$ (chloroacetone)

The carbonyl compounds and its precursors can be a mixture of compounds described above. For example, the mixture can be a carbonyl compound or a precursor such as, for example, trioxane which is known to thermally revert to formaldehyde at elevated temperatures, metaldehyde which is known to thermally revert to acetaldehyde at elevated temperatures, or an alcohol that may be converted to the aldehyde by dehydrogenation of the alcohol to an aldehyde by any known methods. An example of such a conversion to aldehyde from alcohol is described below. An example of a source of carbonyl compounds maybe a mixture of hydroxyacetaldehyde and other aldehydes and ketones produced from fast pyrolysis oil such as described in "Fast Pyrolysis and Bio-oil Upgrading, Biomass-to-Diesel Workshop", Pacific Northwest National Laboratory, Richland, Wash., Sep. 5-6, 2006. The carbonyl compounds and its precursors can also be a mixture of ketones and/or aldehydes with or without alcohols that may be converted to ketones and/or aldehydes, preferably in the range of 1 to 7 carbon atoms.

The preparation of α-hydroxysulfonic acids by the combination of an organic carbonyl compounds, $SO_2$ and water is a general reaction and is illustrated in equation 2 for acetone.

The α-hydroxysulfonic acids appear to be as strong as, if not stronger than, HCl since an aqueous solution of the adduct has been reported to react with NaCl freeing the weaker acid, HCl (see U.S. Pat. No. 3,549,319).

The reaction in equation 1 is a true equilibrium, which results in facile reversibility of the acid. That is, when heated, the equilibrium shifts towards the starting carbonyl, sulfur dioxide, and water (component form). If the volatile components (e.g. sulfur dioxide) are allowed to depart the reaction mixture via vaporization or other methods, the acid reaction completely reverses and the solution becomes effectively neutral. Thus, by increasing the temperature and/or lowering the pressure, the sulfur dioxide can be driven off and the reaction completely reverses due to Le Chatelier's principle, the fate of the carbonyl compound is dependent upon the nature of the material employed. If the carbonyl is also volatile (e.g. acetaldehyde), this material is also easily removed in the vapor phase. Carbonyl compounds such as benzaldehyde, which are sparingly soluble in water, can form a second organic phase and be separated by mechanical means. Thus, the carbonyl can be removed by conventional means, e.g., continued application of heat and/or vacuum, steam and nitrogen stripping, solvent washing, centrifugation, etc. Therefore, the formation of these acids is reversible in that as the temperature is raised, the sulfur dioxide and/or aldehyde and/or ketone can be flashed from the mixture and condensed or absorbed elsewhere in order to be recycled. These reversible acids, which are approximately as strong as strong mineral acids, are effective in biomass treatment reactions.

These treatment reactions produce very few of the undesired byproducts, such as furfurals, produced by other conventional mineral acids at higher temperatures. Additionally, since the acids are effectively removed from the reaction mixture following treatment, neutralization with base to complicate downstream processing is substantially avoided. The ability to reverse and recycle these acids also allows the use of higher concentrations than would otherwise be economically or environmentally practical. As a direct result, the temperature employed in biomass treatment can be reduced to diminish the formation of byproducts such as furfural or hydroxymethylfurfural.

It has been found that the position of the equilibrium given in equation 1 at any given temperature and pressure is highly influenced by the nature of the carbonyl compound employed, steric and electronic effects having a strong influence on the thermal stability of the acid. More steric bulk around the carbonyl tending to favor a lower thermal stability of the acid form. Thus, one can tune the strength of the acid and the temperature of facile decomposition by the selection of the appropriate carbonyl compound.

In one embodiment, the acetaldehyde starting material to produce the alpha-hydroxysulfonic acids can be provided by converting ethanol, produced from the fermentation of the treated biomass of the invention process, to acetaldehyde by dehydrogenation or oxidation. Such processes are described in US20130196400 which disclosure is herein incorporated by reference in its entirety.

As used herein, the term "biomass" means organic materials produced by plants (e.g., leaves, roots, seeds and stalks). Common sources of biomass include: agricultural wastes (e.g., corn stalks, straw, seed hulls, sugarcane leavings, bagasse, nutshells, and manure from cattle, poultry, and hogs); wood materials (e.g., wood or bark, sawdust, timber slash, and mill scrap); municipal waste (e.g., waste paper and yard clippings); and energy crops (e.g., poplars, willows, switch grass, alfalfa, prairie bluestream, corn, soybean, algae and seaweed). The term "biomass" also refers to the primary building blocks of all the above, including, but not limited to, saccharides, lignins, celluloses, hemicelluloses, and starches. The term "polysaccharides" refers to polymeric carbohydrate structures, of repeating units (either mono- or di-saccharides) joined together by glycosidic bonds. These structures are often linear, but may contain various degrees of branching. Examples include storage polysaccharides such as starch and glycogen, and structural polysaccharides such as cellulose and chitin. The biomass is typically preprocessed to suitable particles size that may include grinding. Not intending to restrict the scope of the invention, it is typically found that it is easier to process smaller particles of biomass. Biomass that is size reduced to facilitate handling (e.g. less than 1.3 cm) are particularly susceptible materials.

Various factors affect the conversion of the biomass feedstock in the hydrolysis reaction. The carbonyl compound or incipient carbonyl compound (such as trioxane) with sulfur dioxide and water should be added to in an amount and under conditions effective to form alpha-hydroxysulfonic acids. The temperature and pressure of the hydrolysis reaction should be in the range to form alpha-hydroxysulfonic acids and to hydrolyze biomass into fermentable sugars. The amount of carbonyl compound or its precursor and sulfur dioxide should be to produce alpha-hydroxysulfonic acids in the range from about 1 wt. %, preferably from about 5 wt. %, to about 55 wt. %, preferably to about 40 wt. %, more preferably to about 20 wt. %, based on the total solution. For the reaction, excess sulfur dioxide is not necessary, but any excess sulfur dioxide may be used to drive the equilibrium in eq. 1 to favor the acid form at elevated temperatures. The contacting conditions of the hydrolysis reaction may be conducted at temperatures preferably at least from about 50° C. depending on the alpha-hydroxysulfonic acid used, although such temperature may be as low as room temperature depending on the acid and the pressure used. The contacting condition of the hydrolysis reaction may range preferably up to and including about 150° C. depending on the alpha-hydroxysulfonic acid used. In a more preferred condition the temperature is at least from about 80° C., most preferably at least about 100° C. In a more preferred condition the temperature range up to and including about 90° C. to about 120° C. The reaction is preferably conducted at as low a pressure as possible, given the requirement of containing the excess sulfur dioxide. The reaction may also be conducted at a pressure as low as about 0.1 bara, preferably from about 3 bara, to about pressure of as high as up to 11 bara. The temperature and pressure to be optimally utilized will depend on the particular alpha-hydroxysulfonic acid chosen and optimized based on economic considerations of metallurgy and containment vessels as practiced by those skilled in the art.

Numerous methods have been utilized by those skilled in the art to circumvent these obstacles to mixing, transport and heat transfer. Thus weight percentage of biomass solids to total liquids (consistency) may be as low as 1% or higher depending on the apparatus chosen and the nature of the biomass (even as high as 33% if specialized equipment is developed or used). The solids percent is weight percent of dry solids basis and the wt. % liquids contains the water in the biomass. In the preferred embodiment, where a more conventional equipment is desired, then the consistency is from at least 1 wt. %, preferably at least about 2 wt. %, more preferably at least about 8 wt. %, up to about 25 wt. %, preferably to about 20 wt. %, more preferably to about 15 wt. %.

The temperature of the hydrolysis reaction can be chosen so that the maximum amount of extractable carbohydrates are hydrolyzed and extracted as fermentable sugar (more preferably pentose and/or hexose) or monosaccharide from the biomass feedstock while limiting the formation of degradation products. The temperatures required for successful pretreatment are controlled by the reaction time, the pH of the solution (acid concentration), and the reaction temperature. Thus as the acid concentration is raised, the temperature may be reduced and/or the reaction time extended to accomplish the same objective. The advantages of lowering the reaction temperature are that the fragile monomeric sugars are protected from degradation to dehydrated species such as furfurals and that the lignin sheath is not dissolved or melted and re-deposited upon the biomass. If high enough levels of acid are employed, temperatures can be reduced below the point at which sugar degradation or lignin deposition are problematic; this in turn is made possible through the use of reversible α-hydroxysulfonic acids. In such a low temperature process it becomes possible to recycle a sugars mixture from the back of a pretreatment process to the front of a pretreatment process. This allows the sugars to build to a high steady state value while still handling a pumpable slurry through the pretreatment process. Such a process is outlined in the scheme below. In this process biomass, water, and α-hydroxysulfonic acid are combined in an acid hydrolysis step and reacted to effect biomass pretreatment. The acids are separated from the reaction mixture as described above and recycled to the pretreatment reactor. Then a concentrated high solids/liquid mixture (wet solid stream) is separated from the bulk liquid, which is recycled to the reactor as well. In this manner the biomass to liquids ratio is set by the feed ratio of these components and the optimized target of wet biomass to move into enzymatic hydrolysis.

In some embodiments, a plurality of reactor vessels may be used to carry out the hydrolysis reaction. These vessels may have any design capable of carrying out a hydrolysis reaction. Suitable reactor vessel designs can include, but are not limited to, batch, trickle bed, co-current, counter-current, stirred tank, down flow, or fluidized bed reactors. Staging of reactors can be employed to arrive the most economical solution. The remaining biomass feedstock solids may be optionally separated from the liquid stream to allow more severe processing of the recalcitrant solids or pass directly within the liquid stream to further processing that may include enzymatic hydrolysis, fermentation, extraction, distillation and/or hydrogenation. In another embodiment, a series of reactor vessels may be used with an increasing temperature profile so that a desired sugar fraction is extracted in each vessel. The outlet of each vessel can then be cooled prior to combining the streams, or the streams can be individually fed to the next reaction for conversion.

Suitable reactor designs can include, but are not limited to, a backmixed reactor (e.g., a stirred tank, a bubble column, and/or a jet mixed reactor) may be employed if the viscosity and characteristics of the partially digested bio-based feedstock and liquid reaction media is sufficient to operate in a regime where bio-based feedstock solids are suspended in an excess liquid phase (as opposed to a stacked pile digester). It is also conceivable that a trickle bed reactor could be employed with the biomass present as the stationary phase and a solution of α-hydroxysulfonic acid passing over the material.

In some embodiments, the reactions described below are carried out in any system of suitable design, including systems comprising continuous-flow (such as CSTR and plug flow reactors), batch, semi-batch or multi-system vessels and reactors and packed-bed flow-through reactors. For reasons strictly of economic viability, it is preferable that the invention is practiced using a continuous-flow system at steady-state equilibrium. In one advantage of the process in contrast with the dilute acids pretreatment reactions where residual acid is left in the reaction mixture (<1% wt. sulfuric acid), the lower temperatures employed using these acids (5 to 20% wt.) results in substantially lower pressures in the reactor resulting in potentially less expensive processing systems such as plastic lined reactors, duplex stainless reactors, for example, such as 2205 type reactors.

Since biomass contains caustic inorganic materials (such as calcium and potassium), we have found that the formation of the anion salt of α-hydroxysulfonic acid represent the largest "loss" of the α-hydroxysulfonic acid in the reversible acid pretreatment process. When α-hydroxysulfonic acid encounters a basic species, such as a carbonate, the anionic salt form of the acid is generated. This acid salt is not reversible as the α-hydroxysulfonic acid must be in the protonic form to revert to primary components.

We have found that by titrating the α-hydroxysulfonic acid salt with strong mineral acid and then reverting the α-hydroxysulfonic acid as its primary components, the acid components can be recovered virtually quantitatively providing for a cost reduction in the reversible acid pretreatment process. Preferably the amount of mineral acid added is a small amount that will not interfere with subsequent enzyme hydrolysis and fermentation reactions.

The strong mineral acid should have sufficient pKa to protonate the α-hydroxysulfonic acid salt. Preferably, the mineral acids have a pKa of 7.5 or less, more preferably 3.5 or less. Such mineral acid may include, for example, sulfuric acid, hydrogen sulfate, phosphoric acid, dihydrogen phosphate, and hydrochloric acid.

By adding about a molar equivalent amount of a mineral acid (such as for example, hydrochloric, sulfuric or phosphoric acid) to a solution of salts of alfa-hydroxysulfonic acids, an equilibrium can be achieved between the protonic and mineral salt versions of the acids. By the term about a molar equivalent (based on proton), the molar equivalent may be ±20%. In some instances, a partial titration may be desirable, In such case, less than full molar equivalent of the mineral acid may be used. If residual acidity is desired, excess mineral acid may be added. The mineral acid can be added as low as 0.1 equivalent to 1.2 equivalent to the salt of alfa-hydroxysulfonic acids. As only the alfa-hydroxysulfonic acid is reversible to volatile components, all of the alpha-hydroxysulfonic acid, up to the equivalent amount of mineral acid, can be recovered and the corresponding salt of the mineral acid is formed.

For example, when the potassium salt of alpha-hydroxyethanesulfonic acid (HESA) is treated with an equivalent of sulfuric (a divalent acid), phosphoric (a divalent strong acid), or hydrochloric acid (a monovalent acid), the HESA can be flashed overhead as $SO_2$ and acetaldehyde leaving potassium sulfate, potassium monohydrogen phosphate, or potassium chloride in solution. When HESA is recovered overhead, the pH of the salt solution rises to what it was prior to the addition of the mineral acid.

The reaction (titration) of the α-hydroxysulfonic acid salt with strong mineral acid and then reverting the α-hydroxysulfonic acid as its primary components is illustrated in equation 3 for calcium salt of α-hydroxysulfonic acid.

Figure 1:
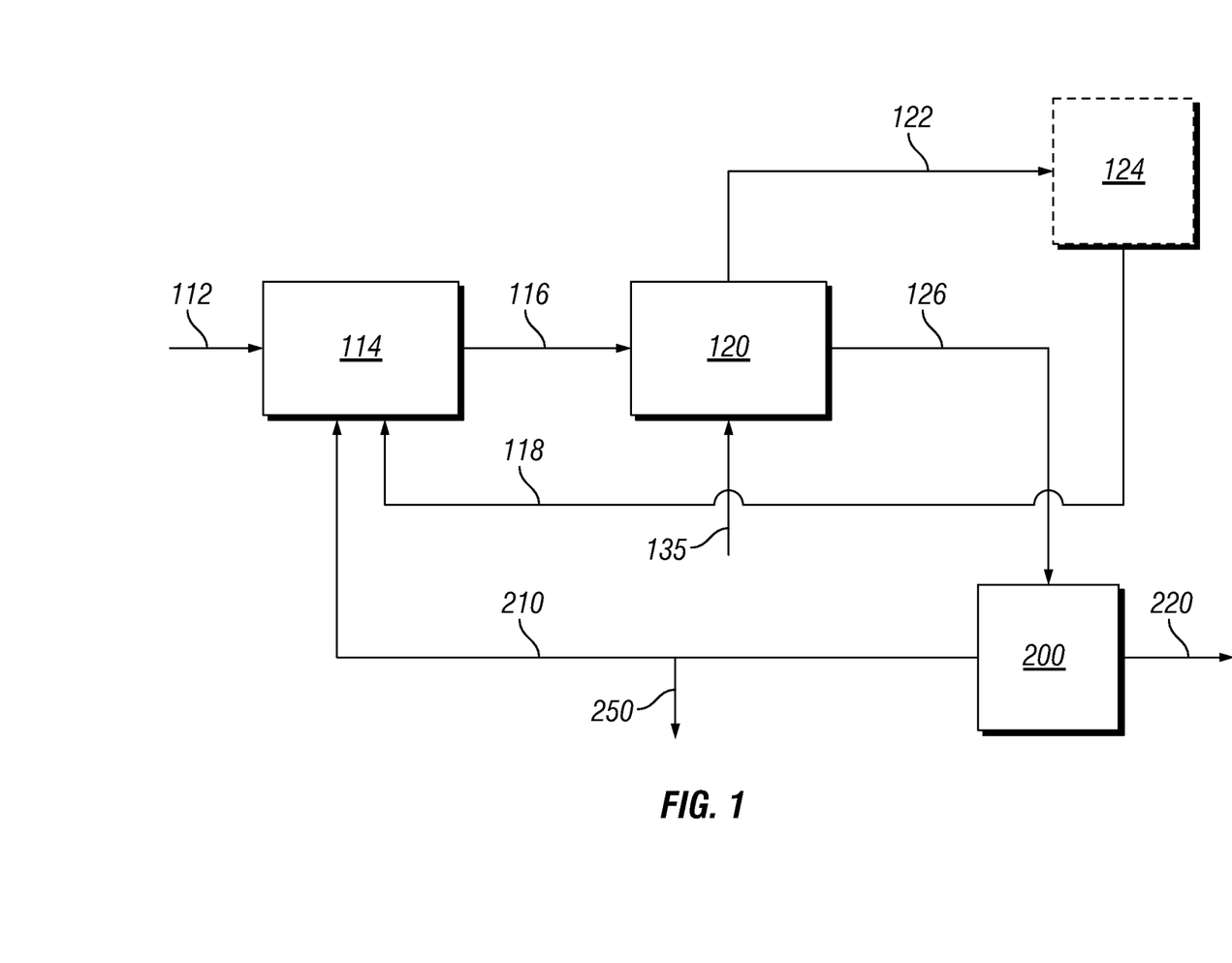
FIG. 1 schematically illustrates a block flow diagram of an embodiment of biomass treatment process of the invention.

FIG. 1 shows an embodiment of the present invention for the improved recovery of the α-hydroxysulfonic acid for the process of converting biomass into sugars or monossacharides. In this embodiment, a biomass feedstock 112 is introduced to a hydrolysis reaction system 114 along with a recycle stream 118. The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one fermentable sugar, at least one α-hydroxysulfonic acid, and at least one salt of α-hydroxysulfonic acid is introduced to acid removal system 120 where the acid is removed in its component form then is recovered 122 (and optionally scrubbed 124) and produces a product stream 126. A mineral acid 135 is introduced to the acid removal system 116 in an amount sufficient to titrate at least a portion of the salt of α-hydroxysulfonic acid (preferably the amount is a small amount that will not interfere with subsequent enzyme hydrolysis and fermentation reactions). Optionally, instead of or in addition to introducing the mineral acid to the acid removal system, the mineral acid 135 may be added to the reacted product stream 116 before the acid removal step 120 (not shown). The recovered acids are recycled via stream 118 to the hydrolysis reaction system 114. The product stream 126 contains at least one fermentable sugar (e.g., pentose and optionally hexose) or at least one monosaccharide substantially without the alpha-hydroxysulfonic acids, preferably in any form. Optionally, at least a portion of the liquid on product stream 116 containing α-hydroxysulfonic acid can be recycled to the hydrolysis reaction system 114 (not shown). The product stream 126 is provided to a separation system 200 where a high solids/liquid mixture can be separated from the acid-removed product stream to form a wet solids stream 220 containing undissolved solids containing cellulose, and a bulk liquid stream 210 that may constitute up to 20 to 80 wt. % of the liquid from the acid-removed product stream that contains fermentable sugar (e.g., pentose and optionally hexose) or monosaccharides. At least a portion of the bulk liquid stream 210 is recycled to the hydrolysis reaction system. A portion of the bulk liquid stream 210 that contains fermentable sugar or monosaccharide can optionally be removed, 250, and further processed to produce biofuel components or other chemicals. Required make up water can be introduced to the primary pretreatment system 114 or in numerous other locations to achieve desired results. For instance, required make up water could be introduced into the solids/liquid separation step 200 in a manner to produce a rinsed biomass, allowing the predominental pentose stream to be processed as a separate stream, 250.

Figure 2:
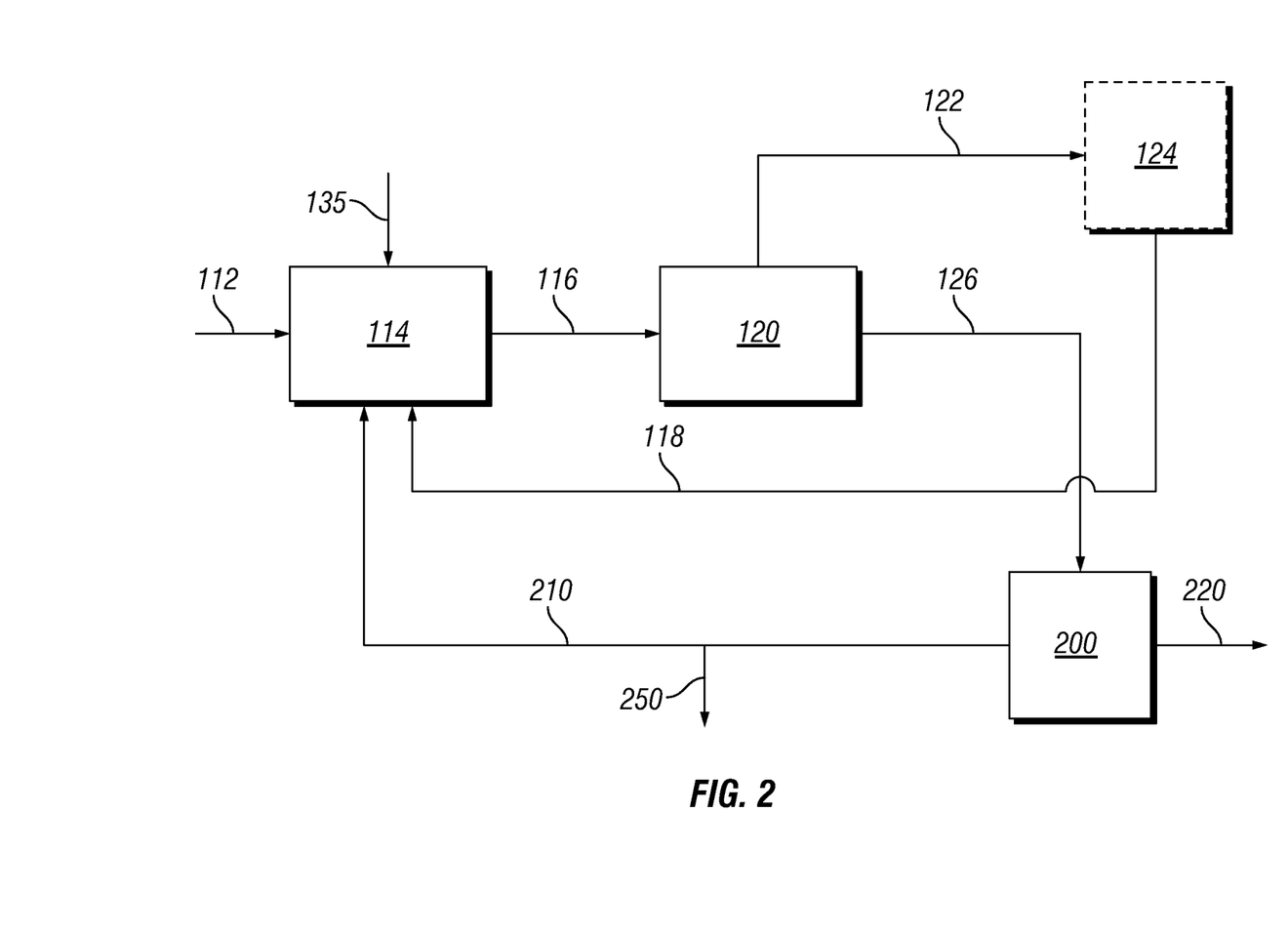
FIG. 2 schematically illustrates another block flow diagram of an embodiment of biomass treatment process of the invention.

FIG. 2 shows an embodiment of the present invention for the improved recovery of the α-hydroxysulfonic acid for the process of converting biomass into sugars or monossacharides. In this embodiment, a biomass feedstock 112 is introduced to a hydrolysis reaction system 114 along with a recycle stream 118 and a small amount of mineral acid 135 (a small amount that will serve to just neutralize the caustic content of the biomass, but not interfere with subsequent enzyme hydrolysis and fermentation reactions). The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one fermentable sugar or monossachride, at least one α-hydroxysulfonic acid, and at least one salt of α-hydroxysulfonic acid is introduced to acid removal system 120 where the acid is removed in its component form then is recovered 122 (and optionally scrubbed 124) and produces a product stream 126. The recovered acids are recycled via stream 118 to the hydrolysis reaction system 114. The product stream 126 contains at least one fermentable sugar (e.g., pentose and optionally hexose) or at least one monosaccharide substantially without the alpha-hydroxysulfonic acids. Optionally, at least a portion of the liquid on product stream 116 containing α-hydroxysulfonic acid can be recycled to the hydrolysis reaction system 114 (not shown). The product stream 126 is provided to a separation system 200 where a high solids/liquid mixture can be separated from the acid-removed product stream to form a wet solids stream 220 containing undissolved solids containing cellulose, and a bulk liquid stream 210 that may constitute up to 20 to 80 wt. % of the liquid from the acid-removed product stream that contains fermentable sugar (e.g., pentose and optionally hexose) or monosaccharides. At least a portion of the bulk liquid stream 210 is recycled to the hydrolysis reaction system. A portion of the bulk liquid stream 210 that contains fermentable sugar or monosaccharide can optionally be removed, 250, and further processed to produce biofuel components or other chemicals. Required make up water can be introduced to the primary pretreatment system 114 or in numerous other locations to achieve desired results. For instance, required make up water could be introduced into the solids/liquid separation step 200 in a manner to produce a rinsed biomass, allowing the predominental pentose stream to be processed as a separate stream, 250.

Figure 3:
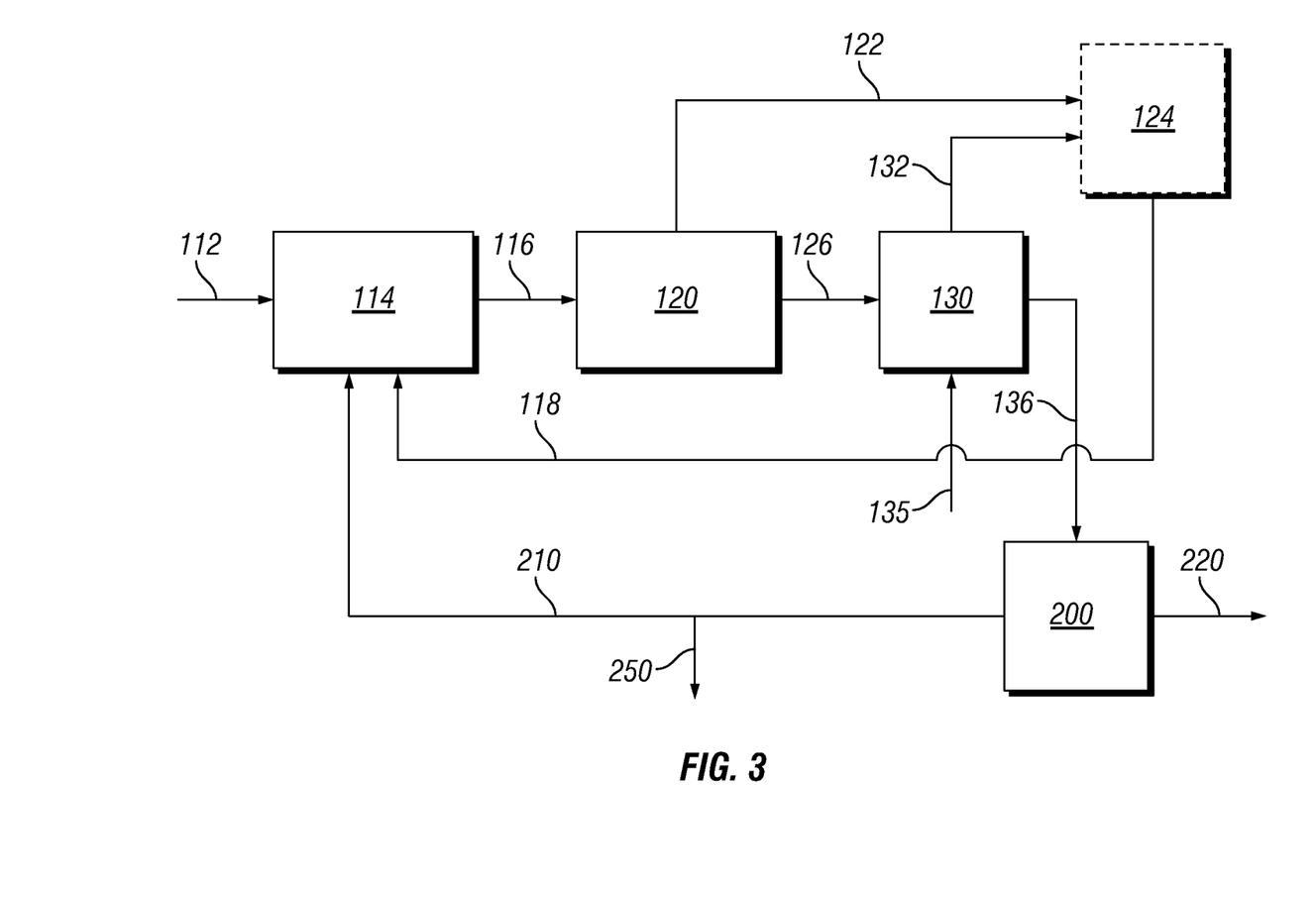
FIG. 3 schematically illustrates another block flow diagram of an embodiment of biomass treatment process of the invention.

FIG. 3 shows an embodiment of the present invention for the improved recovery of the α-hydroxysulfonic acid for the process of converting biomass into sugars or monossacharides. In this embodiment, a biomass feedstock 112 is introduced to a hydrolysis reaction system 114 along with a recycle stream 118. The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one fermentable sugar, at least one α-hydroxysulfonic acid, and at least one salt of α-hydroxysulfonic acid is introduced to acid removal system 120 where the acid is removed in its component form then is recovered 122 (and optionally scrubbed 124) and produces a product stream 126. A mineral acid 135 is introduced to product stream 126 in a titration (or mineral acid reaction) step 130 in an amount sufficient to titrate at least a portion of the salt of α-hydroxysulfonic acid (preferably the amount is a small amount that will not interfere with subsequent enzyme hydrolysis and fermentation reactions). The acid is removed from the titration step in its component form then is recovered 132 (and optionally scrubbed 124) and produces a second product stream 136. The recovered acids are recycled via stream 118 to the hydrolysis reaction system 114. The product stream 136 contains at least one fermentable sugar (e.g., pentose and optionally hexose) or at least one monosaccharide substantially without the alpha-hydroxysulfonic acids or salts of the alpha-hydroxysulfonic acids. Optionally, at least a portion of the liquid on product stream 116 containing α-hydroxysulfonic acid can be recycled to the hydrolysis reaction system 114 (not shown). The second product stream 136 is provided to a separation system 200 where a high solids/liquid mixture can be separated from the acid-removed product stream to form a wet solids stream 220 containing undissolved solids containing cellulose, and a bulk liquid stream 210 that may constitute up to 20 to 80 wt. % of the liquid from the acid-removed product stream that contains fermentable sugar (e.g., pentose and optionally hexose) or monosaccharides. At least a portion of the bulk liquid stream 210 is recycled to the hydrolysis reaction system. A portion of the bulk liquid stream 210 that contains fermentable sugar or monosaccharide can optionally be removed, 250, and further processed to produce biofuel components or other chemicals. Required make up water can be introduced to the primary pretreatment system 114 or in numerous other locations to achieve desired results. For instance, required make up water could be introduced into the solids/liquid separation step 200 in a manner to produce a rinsed biomass, allowing the predominental pentose stream to be processed as a separate stream, 250.

Figure 4:
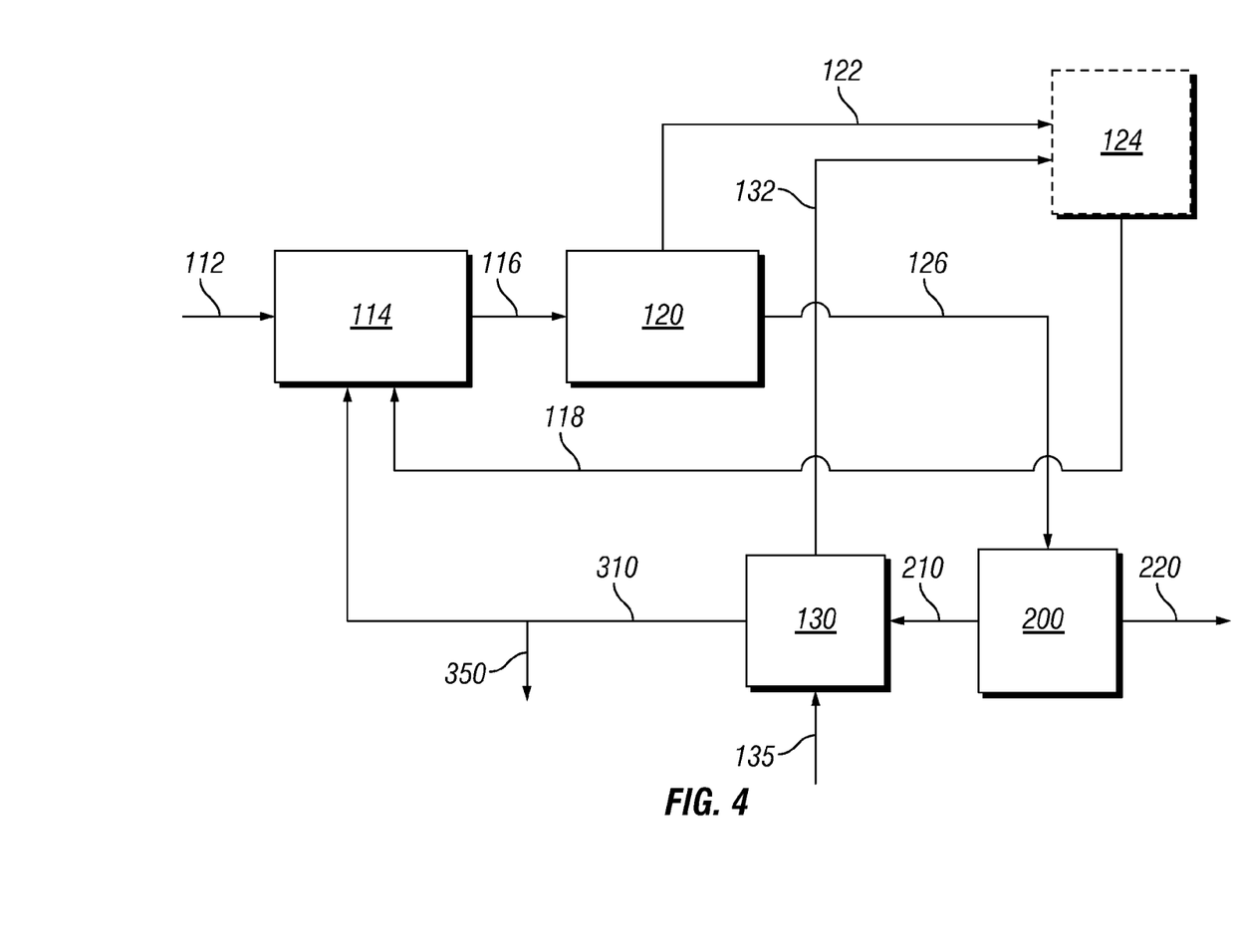
FIG. 4 schematically illustrates another block flow diagram of an embodiment of biomass treatment process of the invention.

FIG. 4 shows an embodiment of the present invention for the improved recovery of the α-hydroxysulfonic acid for the process of converting biomass into sugars or monossacharides. In this embodiment, a biomass feedstock 112 is introduced to a hydrolysis reaction system 114 along with a recycle stream 118. The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one fermentable sugar, at least one α-hydroxysulfonic acid, and at least one salt of α-hydroxysulfonic acid is introduced to acid removal system 120 where the acid is removed in its component form then is recovered 122 (and optionally scrubbed 124) and produces a product stream 126. The recovered acids are recycled via stream 118 to the hydrolysis reaction system 114. The product stream 126 contains at least one fermentable sugar (e.g., pentose and optionally hexose) or at least one monosaccharide substantially without the alpha-hydroxysulfonic acids or salts of the alpha-hydroxysulfonic acids. Optionally, at least a portion of the liquid on product stream 116 containing α-hydroxysulfonic acid can be recycled to the hydrolysis reaction system 114 (not shown). The second product stream 126 is provided to a separation system 200 where a high solids/liquid mixture can be separated from the acid-removed product stream to form a wet solids stream 220 containing undissolved solids containing cellulose, and a bulk liquid stream 210 that may constitute up to 20 to 80 wt. % of the liquid from the acid-removed product stream that contains fermentable sugar (e.g., pentose and optionally hexose) or monosaccharides and the salt of alpha-hydroxysulfonic acids. A mineral acid 135 is introduced to at least a portion of the bulk liquid stream 210 in a titration (or mineral acid reaction) step 130 in an amount sufficient to titrate at least a portion of the salt of α-hydroxysulfonic acid (preferably the amount is a small amount that will not interfere with subsequent enzyme hydrolysis and fermentation reactions). The alpha-sulfonic acid is removed from the titration step in its component form then is recovered 132 (and optionally scrubbed 124) and produces a product recycle stream 310 substantially free of the salt of the alpha-hydroxysulfonic acid recycled to the hydrolysis reaction system. A portion of the alpha-hydroxysulfonic acid salt removed bulk liquid stream 310 that contains fermentable sugar or monosaccharide can optionally be removed, 350, and further processed to produce biofuel components or other chemicals. Required make up water can be introduced to the primary pretreatment system 114 or in numerous other locations to achieve desired results. For instance, required make up water could be introduced into the solids/liquid separation step 200 in a manner to produce a rinsed biomass, allowing the wet solid stream containing predominental cellulose to be processed as a separate stream, 220.

Figure 5:
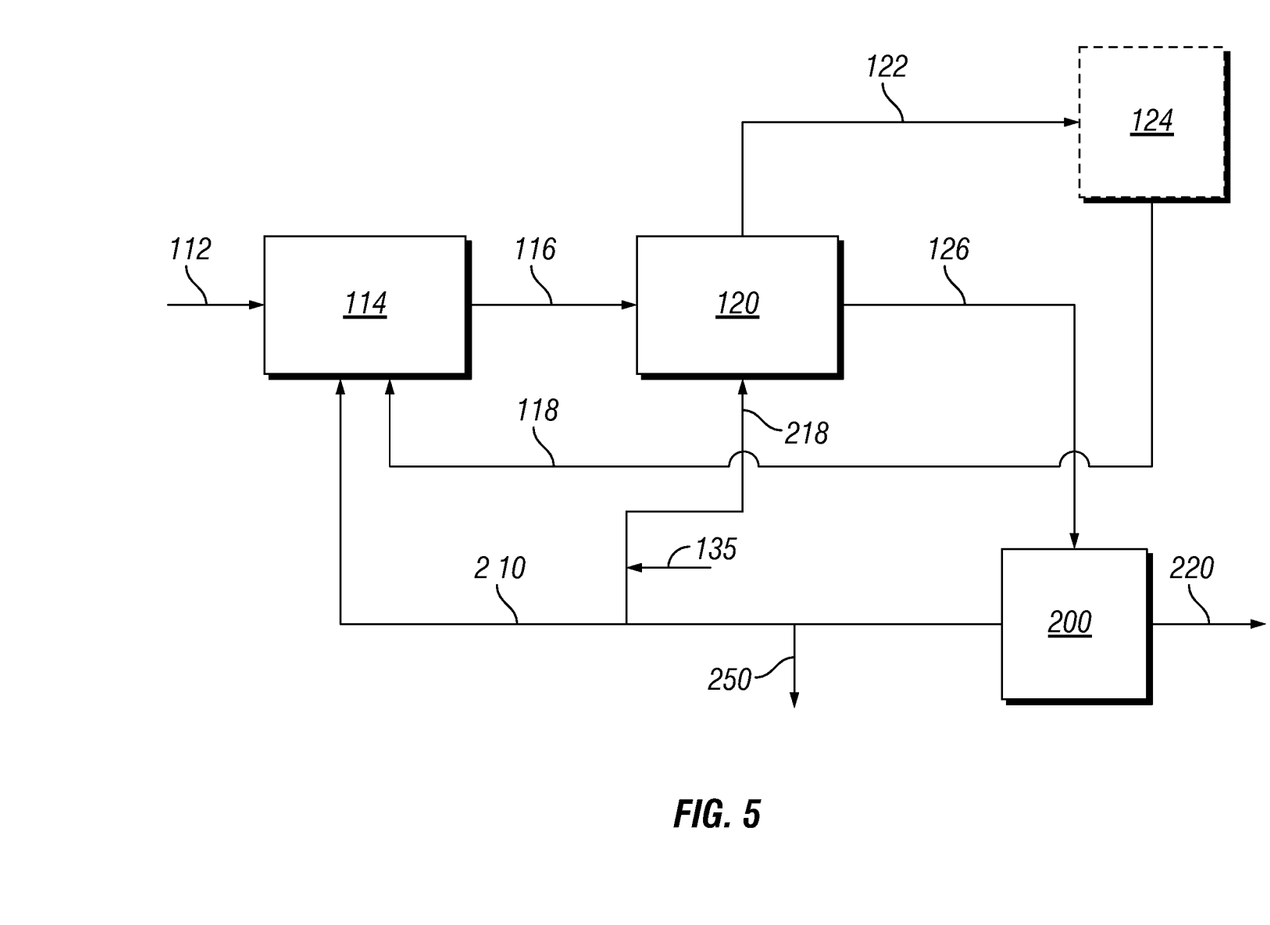
FIG. 5 schematically illustrates another block flow diagram of an embodiment of biomass treatment process of the invention.

FIG. 5 shows an embodiment of the present invention for the improved recovery of the α-hydroxysulfonic acid for the process of converting biomass into sugars or monossacharides. In this embodiment, a biomass feedstock 112 is introduced to a hydrolysis reaction system 114 along with a recycle stream 118. The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one fermentable sugar, at least one α-hydroxysulfonic acid, and at least one salt of α-hydroxysulfonic acid is introduced to acid removal system 120 where the acid is removed in its component form then is recovered 122 (and optionally scrubbed 124) and produces a product stream 126. The product stream 126 contains at least one fermentable sugar (e.g., pentose and optionally hexose) or at least one monosaccharide substantially without the alpha-hydroxysulfonic acids. Optionally, at least a portion of the liquid on product stream 116 containing α-hydroxysulfonic acid can be recycled to the hydrolysis reaction system 114 (not shown). The product stream 126 is provided to a separation system 200 where a high solids/liquid mixture can be separated from the acid-removed product stream to form a wet solids stream 220 containing undissolved solids containing cellulose, and a bulk liquid stream 210 that may constitute up to 20 to 80 wt. % of the liquid from the acid-removed product stream that contains fermentable sugar (e.g., pentose and optionally hexose) or monosaccharides. At least a first portion of the bulk liquid stream 210 is recycled to the hydrolysis reaction system 114 and a second portion of the bulk liquid stream 218 is recycled to the acid removal system 120. A mineral acid 135 is introduced to the recycle stream 218 where it is delivered to the acid removal system with the recycle stream in an amount sufficient to titrate at least a portion of the salt of α-hydroxysulfonic acid (preferably the amount is a small amount that will not interfere with subsequent enzyme hydrolysis and fermentation reactions). The recovered acids are recycled via stream 118 to the hydrolysis reaction system 114. A portion of the bulk liquid stream 210 that contains fermentable sugar or monosaccharide can optionally be removed, 250, and further processed to produce biofuel components or other chemicals. Required make up water can be introduced to the primary pretreatment system 114 or in numerous other locations to achieve desired results. For instance, required make up water could be introduced into the solids/liquid separation step 200 in a manner to produce a rinsed biomass, allowing the predominental pentose stream to be processed as a separate stream, 250.

In yet another embodiment (not shown as figures), the process can be used with recycled alpha-hydroxysulfonic acid without any of the product recycled via stream 210 or stream 310 in any of the embodiments described above.

The treatment reaction product contains fermentable sugar or monosaccharides, such as pentose and/or hexose that is suitable for further processing. Optionally, at least a portion of the liquid stream containing the residual alpha-hydroxysulfonic acid from the fermentable sugar containing product stream may be recycled to the treatment reaction. The residual alpha-hydroxysulfonic acid can be removed by application of heat and/or vacuum from the fermentable sugar containing product stream to reverse the formation of alpha-hydroxysulfonic acid to its starting material to produce a stream containing fermentable sugar substantially free of the α-hydroxysulfonic acid. In particular, the product stream is substantially free of alpha-hydroxysulfonic acid, meaning no more than about 2 wt. % is present in the product stream, preferably no more than about 1 wt. %, more preferably no more than about 0.2 wt. %, most preferably no more than about 0.1 wt. % present in the product stream The temperature and pressure will depend on the particular alpha-hydroxysulfonic acid used and minimization of temperatures employed are desirable to preserve the sugars obtain in treatment reactions. Typically the removal may be conducted at temperatures in the range from about 50° C., preferably from about 80° C., more preferably from 90° C., to about 110° C., up to about 150° C. The pressure should be such that the α-hydroxysulfonic acid is flashed in its component form at the temperature for removal of the acid. This pressure should be at or above the pressure of the saturated steam at such temperature but low enough to flash the α-hydroxysulfonic acid in its component form. For examples, the pressure may be in the range of from about 0.1 bara, to about 5 bara, more preferably from 0.5 bara to about 2 bara. In general, the α-hydroxysulfonic acid treatment step (b) should be under conditions to maintain α-hydroxysulfonic acid to be in the treatment mixture at the temperature and pressure in order to hydrolyze the biomass, whereas the temperature and pressure of the α-hydroxysulfonic acid will be such that the α-hydroxysulfonic acid is flashed in its component form. Typically, (i) the temperature is higher than step (b), (ii) the pressure is less than step (b) or (iii) the temperature is higher and pressure is lower than step (b). It is contemplated that the temperature may not be higher than step (b) so long as pressure is lower than step (b) sufficient to flash the α-hydroxysulfonic acid.

It can be appreciated by a person skill in the art that the treatment reaction 114 and the removal of the acid 120 can occurred in the same vessel or a different vessel or in a number of different types of vessels depending on the reactor configuration and staging as long as the system is designed so that the reaction is conducted under condition favorable for the formation and maintenance of the alpha-hydroxysulfonic acid and removal favorable for the reverse reaction (as components). As an example, the reaction in the reactor vessel 114 can be operated at approximately 100° C. and a pressure of 3 bara in the presence of alpha-hydroxyethanesulfonic acid and the removal vessel 120 can be operated at approximately 110° C. and a pressure of 0.5 bara. It is further contemplated that the reversion can be favored by the reactive distillation of the formed alpha-hydroxysulfonic acid. In the recycling of the removed acid, optionally additional carbonyl compounds, $SO_2$, and water may be added as necessary. The removed starting material and/or alpha-hydroxysulfonic acid may be condensed and/or scrubbed by contact with water and recycled to the reaction system 114 as components or in its recombined form.

The preferable residence time of the biomass to contact with the α-hydroxysulfonic acid in the hydrolysis reaction system may be in the range of about 5 minutes to about 4 hours, most preferably about 15 minutes to about 1 hour.

The separation system can be carried out by any separation method to separate wet solids and liquids. Examples of suitable separation method, for example, may include centrifugal force, filtration, decantation, and other like methods.

The an acid-removed product may be further processed to produce at least one organic compound such as described below. The processing may be carried out for the α-hydroxysulfonic acid treated product stream, liquid stream or the wet solids stream. The at least one compound may be alcohols such as described below, diols, furfurals, and hydrocarbons. In one embodiment, the cellulose containing product stream can further be hydrolyzed by other methods, for example by enzymes to further hydrolyze the biomass to sugar products containing pentose and hexose (e.g., glucose) and fermented to produce alcohols such as disclosed in U.S. Publication No. 2009/0061490 and U.S. Pat. No. 7,781,191 which disclosures are hereby incorporated by reference.

In yet another embodiment, the fermentable sugars or monosaccharides can be converted to higher hydrocarbons as a biofuel component using catalytic hydrogenation and condensation techniques rather than further hydrolysis by enzyme and fermentation. Typically the fermentable sugar containing product is contacted with hydrogen in the presence of a hydrogenolysis catalyst to form a plurality of oxygenated intermediates, and then further processing the oxygenated intermediates to produce a fuel blend in one or more processing reactions. In an embodiment, a condensation reaction can be used along with other reactions to generate a fuel blend and may be catalyzed by a catalyst comprising acid or basic functional sites, or both to product a liquid fuel. As used herein, the term "higher hydrocarbons" refers to hydrocarbons having an oxygen to carbon ratio less than at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (e.g., oxygen or sulfur) and thus the term "hydrocarbon" may also include substituted hydrocarbons.

In one such example, the fermentable sugar containing product stream may be further processed to produce mixtures of C4+ compounds useful for biofuels such as described in U.S. Publication Nos. US2011/0154721 and US2011/0282115 which disclosures are hereby incorporated by reference. As another such example, the fermentable sugar containing product stream may be further processed to produce mixtures of C4+ compounds useful for biofuels such as described in U.S. Publication No. 20080216391 which disclosure is hereby incorporated by reference. The solid feed may also be suitable for use in fast pyrolysis reactions leading to fuels and chemicals.

The term "fermentable sugar" refers to oligosaccharides and monosaccharides that can be used as a carbon source (e.g., pentoses and hexoses) by a microorganism in a fermentation process. It is contemplated that fermentable sugar may be fermented as described above, but may also be processed by other methods without fermentation to produce fuels as described above. The term "pentose" refers to monosaccharides with five carbon atoms. The term "hexose" refers to monosaccharides with six carbon atoms.

In an enzymatic hydrolysis-fermentation processes the pH of the pretreated feedstock to the enzymatic hydrolysis is typically adjusted so that it is within a range which is optimal for the cellulase enzymes used. Generally, the pH of the pretreated feedstock is adjusted to within a range of about 3.0 to about 7.0, or any pH there between.

The temperature of the treated feedstock is adjusted so that it is within the optimum range for the activity of the cellulase enzymes. Generally, a temperature of about 15° C. to about 100° C., about 20° C. to about 85° C., about 30° C. to about 70° C. preferably or any temperature there between, is suitable for most cellulase enzymes. The cellulases, β-glucosidase and other accessory enzymes required for cellulose hydrolysis are added to the pretreated feedstock, prior to, during, or after the adjustment of the temperature and pH of the aqueous slurry after pretreatment. Preferably the enzymes are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include cellobiohydrolases (CBH), glucobiohydrolases (GBH), endoglucanases (EG), glycosyl hydrolyase family 61 proteins (GH61) and β-glucosidase. By the term "β-glucosidase", it is meant any enzyme that hydrolyzes the glucose dimer, cellobiose, to glucose. In a non-limiting example, a cellulase mixture may include EG, CBH, GH61 and β-glucosidase enzymes.

The enzymatic hydrolysis may also be carried out in the presence of one or more xylanase enzymes. Examples of xylanase enzymes that may also be used for this purpose and include, for examples, xylanase 1,2 (Xyn1 and Xyn2) and β-xylosidase, which are typically present in cellulase mixtures.

The process can be carried out with any type of cellulase enzymes, regardless of their source. Non-limiting examples of cellulases which may be used include those obtained from fungi of the genera *Aspergillus, Humicola*, and *Trichoderma, Myceliophthora, Chrysosporium* and from bacteria of the genera *Bacillus, Thermobifida* and *Thermotoga*. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

The cellulase enzyme dosage is chosen to convert the cellulose of the pretreated feedstock to glucose. For example, an appropriate cellulase dosage can be about 1 to about 100 mg enzyme (dry weight) per gram of cellulose.

In practice, the hydrolysis may carried out in a hydrolysis system, which may include a series of hydrolysis reactors. The number of hydrolysis reactors in the system depends on the cost of the reactors, the volume of the aqueous slurry, and other factors. The enzymatic hydrolysis with cellulase enzymes produces an aqueous sugar stream (hydrolyzate) comprising glucose, unconverted cellulose, lignin and other sugar components. The hydrolysis may be carried out in two stages (see U.S. Pat. No. 5,536,325, which is incorporated herein by reference), or may be performed in a single stage.

In the fermentation system, the aqueous sugar stream is then fermented by one or more than one fermentation microorganism to produce a fermentation broth comprising the alcohol fermentation product useful as biofuels. In the fermentation system, any one of a number of known microorganisms (for example, yeasts or bacteria) may be used to convert sugar to ethanol or other alcohol fermentation products. The microorganisms convert sugars, including, but not limited to glucose, mannose and galactose present in the clarified sugar solution to a fermentation product.

Many known microorganisms can be used in the present process to produce the desired alcohol for use in biofuels. *Clostridia, Escherichia coli* (*E. coli*) and recombinant strains of *E. coli*, genetically modified strain of *Zymomonas mobilis* such as described in U.S. 2003/0162271, U.S. Pat. No. 7,741,119 and U.S. Pat. No. 7,741,084 (which disclosures are herein incorporated by reference) are some examples of such bacteria. The microorganisms may further be a yeast or a filamentous fungus of a genus *Saccharomyces, Kluyveromyces, Candida, Pichia, Schizosaccharomyces, Hansenula, Kloeckera, Schwanniomyces, Yarrowia, Aspergillus, Trichoderma, Humicola, Acremonium, Fusarium*, and *Penicillium*. The fermentation may also be performed with recombinant yeast engineered to ferment both hexose and pentose sugars to ethanol. Recombinant yeasts that can ferment one or both of the pentose sugars xylose and arabinose to ethanol are described in U.S. Pat. No. 5,789,210, U.S. Pat. No. 6,475,768, European Patent EP 1727890, European Patent EPI 863901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631). It is also contemplated that the fermentation organism may also produce fatty alcohols, for example, as described in WO 2008/119082 and PCT/US07/011923 which disclosure is herein incorporated by reference. In another embodiment, the fermentation may be performed by yeast capable of fermenting predominantly C6 sugars for example by using commercially available strains such as Thermosacc and Superstart.

Preferably, the fermentation is performed at or near the temperature and pH optima of the fermentation microorganism. For example, the temperature may be from about 25° to about 55° C., or any amount there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The fermentation may be conducted in batch, continuous or fed-batch modes, with or without agitation. The fermentation system may employ a series of fermentation reactors.

In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

The fermentation system produces an alcohol stream preferably containing at least one alcohol having 2 to 18 carbon atoms. In the recovery system, when the product to be recovered in the alcohol stream is a distillable alcohol, such as ethanol, the alcohol can be recovered by distillation in a manner known to separate such alcohol from an aqueous stream. If the product to be recovered in the alcohol stream is not a distillable alcohol, such as fatty alcohols, the alcohol can be recovered by removal of alcohols as solids or as oils from the fermentation vessel, thus separating from the aqueous effluent stream.

While the invention is susceptible to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

ILLUSTRATIVE EMBODIMENTS

General Methods and Materials

In the examples, the aldehyde or aldehyde precursors were obtained from Sigma-Aldrich Co.

General Procedure for the Formation of α-Hydroxysulfonic Acids.

Aldehydes and ketones will readily react with sulfur dioxide in water to form α-hydroxy sulfonic acids according to the equation 1 above. These reactions are generally rapid and somewhat exothermic. The order of addition ($SO_2$ to carbonyl or carbonyl to $SO_2$) did not seem to affect the outcome of the reaction. If the carbonyl is capable of aldol reactions, preparation of concentrated mixtures (>30% wt.) are best conducted at temperatures below ambient to minimize side reactions. We have found it beneficial to track the course of the reaction using in situ Infrared Spectroscopy (ISIR) employing probes capable of being inserted into pressure reaction vessels or systems. There are numerous manufacturers of such systems such as Mettler Toledo Autochem's Sentinal probe. In addition to being able to see the starting materials: water (1640 $cm^{-1}$), carbonyl (from approx. 1750 $cm^{-1}$ to 1650 $cm^{-1}$ depending on the organic carbonyl structure) and $SO_2$ (1331 $cm^{-1}$), the formation of the α-hydroxysulfonic acid is accompanied by the formation of characteristic bands of the $SO_3^-$ group (broad band around 1200 $cm^{-1}$) and the stretches of the α-hydroxy group (single to multiple bands around 1125 $cm^{-1}$). In addition to monitoring the formation of the α-hydroxy sulfonic acid, the relative position of the equilibrium at any temperature and pressure can be readily assessed by the relative peak heights of the starting components and the acid complex. The definitive presence of the α-hydroxysulfonic acid under biomass hydrolysis conditions can also be confirmed with the ISIR and it is possible to monitor the growth of sugars in the reaction mixture by monitoring the appropriate IR bands.

Examples 1-4

Long term stability tests of α-hydroxyethane sulfonic acid followed by reversal and overhead recovery of the α-hydroxyethane sulfonic acid were carried out.

Into a 2 liter C276 Parr reactor fitted with in situ IR optics was added 1000 grams of a hydroxyethane sulfonic acid (HESA, approx. 5 or 10% wt.) prepared by the dilution of a 40% wt. stock solution of the acid with deionized water. Target concentration was confirmed by proton NMR of the starting mixture integrating over the peaks for water and the acid. Pressure integrity of the reactor system and air atmosphere replacement was accomplished by pressurization with nitrogen to 100 psig where the sealed reactor was held for 15 minutes without loss of pressure followed by venting to atmospheric pressure where the reactor was sealed. The reactor was then heated to 90 to 120° C. and held at target temperature for four hours. During this period of time the in situ IR reveals the presence of HESA, $SO_2$, and acetaldehyde in an equilibrium mixture. The higher temperature runs having the equilibrium shifted more towards the starting components than the lower temperature runs, indicative of a true equilibrium.

At the end of four hours the acid reversal was accomplished via opening the gas cap of the reactor to an overhead condensation system for recovery of the acid and adjusting the reactor temperature to 100° C. This overhead system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with about 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of the α hydroxyethane sulfonic acid. The IR of the overheads revealed that the concentration of the HESA at this point had reached a maximum and then started to decrease due to dilution with condensed water, free of α-hydroxyethane sulfonic acid components, building in the recovery flask. The reactor was then sealed and cooled to room temperature.

The residual liquid in the Parr reactor and the overhead recovered acid was analyzed via proton NMR for HESA concentration. The results are shown in Table 1 below indicating recovery of acid with virtually no residual HESA in the Parr reactor.

TABLE 1

| Example | Starting [HESA] % wt. | Reaction Temp. ° C. | Reversal time (min.) | [HESA] in overhead (% wt.) | Mass overheaded (g.) | % of HESA recovered | Overall Mass Balance % |
|---|---|---|---|---|---|---|---|
| 1 | 10.01 | 90 | 42 | 15.15 | 243.1 | 96.9 | 99.4 |
| 2 | 10.07 | 105 | 39 | 14.33 | 241.4 | 91.3 | 99.3 |
| 3 | 5.11 | 105 | 40 | 7.39 | 255.1 | 94.7 | 99.5 |
| 4 | 5.36 | 120 | 37 | 8.42 | 163.3 | 88.5 | 99.4 |

The main losses were from side reactions. No metal cations were present in this feed. When the anion is present as a salt (all biomass has cations present) major yield loss was observed. The salt has proved to be stable and does not overhead.

Example 5: Reversion of HESA in the Presence of K+

Reversion and recovery of alpha-hydroxy ethane sulfonic acid (HESA) in the presence of $K_2CO_3$ was carried out without biomass present.

Into a 300 ml autoclave equipped with a DiComp IR probe was place 100.2 grams of 19.13% w alpha-hydroxyethane sulfonic acid (verified by proton NMR). 19.13 g HESA equals ~0.152 moles of acid. To this 2.20 g of potassium carbonate ($K_2CO_3$, EMD Millipore 99.0%) was slowly added. This calculates to ~0.032 moles K+. As the soluble potassium salt of the acid was made, carbon dioxide was released to atmosphere. The carbon dioxide vented was assumed to be complete for material balance purposes. A total of 0.21 moles K+ was added per mole of acid. After all of the potassium carbonate was dissolved, the reactor was sealed. It was fitted with heating bands and the stirrer was started (1000 rpm). The system was then purged lightly three times with nitrogen. The sample was heated to 100° C. and held for ~1 hour at temperature.

The reactor was attached to a vapor recovery system comprising a 3 neck 250 ml round bottom flask, submerged in a wet ice bath, and is fitted with a dry ice acetone condenser. 70.0 g of water is charged to the flask prior to the experiment. The vapor recovery system and the reactor are separated by a vent valve.

At the end of the 1 hour period the vent valve between the reactor and leading to the vapor recovery system was slowly opened. The pressure of the reactor was released in 2.5 minutes from 62.5 psig to 0 psig. The reactor was then held at 100° C. for 22 more minutes. At that point, the valve is closed and the vent recovery system removed. The reactor is pressurized with 2.7 barg of nitrogen and allowed to cool room temperature. A total of 51.26 g of material was over headed into the 70 g of water in the vapor recovery system (121.26 g total) during the run. 49.16 g of material was left in the reactor. After subtracting the $CO_2$ initially removed from the system the overall material balance was found to be ~98.7%.

The overall acid recovery was found to be ~94% with a small amount of acid degradation observed by the proton NMR. The overhead liquid analysis found ~11.74% w or 14.23 g of HESA. ~74.4% of the HESA originally present. The bottoms product showed 7.71% w anion (or acid by NMR), or 3.79 g HESA or ~0.03 moles. This is approximately equal to the number of K+ moles (0.032) added at the beginning of the experiment and well within the uncertainties in measurement for the study.

Example 6: Recovery of HESA was Carried Out by Addition of Near Equal Molar Sulfuric Acid to the Calcium HESA Salt and Recovering HESA in the Overhead Into a 300 ml autoclave equipped with a DiComp IR probe was place 153.43 g of total solution containing the calcium salt of HESA. The solution was made from 15 g of HESA as acid and an equal molar concentration of Calcium carbonate. To this salt solution 5.7 g of 98% w sulfuric acid (0.116 moles H+) was slowly added. During the addition of the sulfuric acid, solids were seen to forming at the bottom of the reactor. After the addition of the sulfuric acid was complete, the reactor was sealed. It was fitted with heating bands and the stirrer was started (1000 rpm). The system was then purged lightly three times with nitrogen prior to heating. The sample was then heated to 100° C. and held at 100 C for about 40 minutes. The reactor pressure was approximately 48 psig.

The reactor was attached to a vapor recovery system comprising a 3 neck 250 ml round bottom flask, submerged in a wet ice bath, and is fitted with a dry ice acetone condenser. 70.03 g of water is charged to the flask prior to the experiment. The vapor recovery system and the reactor are separated by a vent valve.

The vent valve was very slowly opened dropping the pressure while maintaining a reactor temperature around 100° C. or slightly higher. After reaching 0 psig for and holding approximately 30 minutes the valve is closed and the vent recovery system removed. The reactor is pressurized with nitrogen and allowed to cool room temperature.

The overall material balance was found to be 98.4%. A total of 15.86 g of material was over headed into the 70.03 g of water in the vapor recovery system (121.26 g total) during the run. The overhead was analyzed to be 15.2% w HESA (13.1 g acid) or 87% overall acid recovery in the overhead.

It should be noted that the same procedure except without the addition of sulfuric acid led to no acid recovery.

Example 7: Recovery of HESA was Carried Out by Addition of Phosphoric Acid to the Calcium HESA Salt and Recovering HESA in the Overhead Into a 300 ml autoclave equipped with a DiComp IR probe was place 153.21 g of total solution containing the calcium salt of HESA. The solution was made from 15.5 g of HESA as acid and an equal molar concentration of Calcium carbonate. To this salt solution 4.29 g of 85% w phosphoric acid (0.112 total moles of H+ if all disassociated) was slowly added. After the addition of the phosphoric acid was complete, the reactor was sealed. It was fitted with heating bands and the stirrer was started (1000 rpm). The system was then purged lightly three times with nitrogen prior to heating. The sample was then heated to 100 C and held at 100 C for about 60 minutes. The reactor pressure was approximately 33 psig.

The reactor was attached to a vapor recovery system comprising a 3 neck 250 ml round bottom flask, submerged in a wet ice bath, and is fitted with a dry ice acetone condenser. 70.03 g of water is charged to the flask prior to the experiment. The vapor recovery system and the reactor are separated by a vent valve.

The vent valve was very slowly opened dropping the pressure while maintaining a reactor temperature around 100° C. or slightly higher. After reaching 0 psig and holding for approximately 60 minutes the valve is closed and the vent recovery system removed. The reactor is pressurized with nitrogen and allowed to cool room temperature. The ISM showed that the HESA anion/acid only went partially away from this exercise.

The overall material balance was found to be 97.0%. A total of 113.62 g of material was over headed into the 70.03 g of water in the vapor recovery system (183.65 g total) during the run. The overhead was analyzed to be 5.74% w HESA (10.54 g acid) or ~67.5% overall acid recovery in the overhead. There was a precipitate in the bottoms.

Example 8: Recovery of HESA by Addition of Phosphoric Acid to the Calcium HESA Salt and Recovering HESA in the Overhead Into a 300 ml autoclave equipped with a DiComp IR probe was place 153.43 g of total solution containing the calcium salt of HESA. The solution was made from 15.0 g of HESA as acid and an equal molar concentration of Calcium carbonate. To this salt solution 6.44 g of 85% w phosphoric acid (~0.0168 total moles of H+ if all disassociated) was slowly added. After the addition of the phosphoric acid was complete, the reactor was sealed. It was fitted with heating bands and the stirrer was started (1000 rpm). The system was then purged lightly three times with nitrogen prior to heating. The sample was then heated to 102 C and held for 2 minutes at this temperature. The reactor pressure was approximately 39 psig. The reactor was attached to a vapor recovery system comprising a 3 neck 250 ml round bottom flask, submerged in a wet ice bath, and is fitted with a dry ice acetone condenser. 70.0 g of water is charged to the flask prior to the experiment. The vapor recovery system and the reactor are separated by a vent valve.

The vent valve was very slowly opened dropping the pressure while maintaining a reactor temperature around 100 C or slightly higher. After reaching 0 psig and holding for approximately 65 minutes the valve is closed and the vent recovery system removed. The reactor is pressurized with nitrogen and allowed to cool room temperature.

The overall material balance was found to be 97.9%. A total of 98.76 g of material was over headed into the 70.03 g of water in the vapor recovery system (168.76 g total) during the run. The overhead was analyzed to be 7.75% w HESA (13.07 g acid) or ~87.65% overall acid recovery in the overhead. There was a precipitate in the bottoms.

Example 9: Recovery of HESA was Carried Out by Addition of Hydrochloric Acid to the Calcium HESA Salt and Recovering HESA in the Overhead Into a 300 ml autoclave equipped with a DiComp IR probe was place 154.22 g of total solution containing the calcium salt of HESA. The solution was made from 14.9 g of HESA as acid and an equal molar concentration of Calcium carbonate. To this salt solution 10.87 g of 37% w hydrochloric acid (~0.011 total moles of H+) was slowly added. After the addition of the hydrochloric acid was complete, the reactor was sealed. It was fitted with heating bands and the stirrer was started (1000 rpm). The system was then purged lightly three times with nitrogen prior to heating. The sample was then heated to 102 C and held for 9 minutes at this temperature. The reactor pressure was approximately 47 psig.

The reactor was attached to a vapor recovery system comprising a 3 neck 250 ml round bottom flask, submerged in a wet ice bath, and is fitted with a dry ice acetone condenser. 70.0 g of water is charged to the flask prior to the experiment. The vapor recovery system and the reactor are separated by a vent valve.

The vent valve was very slowly opened dropping the pressure while maintaining a reactor temperature around 100° C. or slightly higher. After reaching 0 psig and holding for approximately 37 minutes the valve is closed and the vent recovery system removed. The reactor is pressurized with nitrogen and allowed to cool room temperature.

The overall material balance was found to be ~100.5%. A total of 16.91 g of material was over headed into the 70.03 g of water in the vapor recovery system (86.93 g total) during the run. The overhead was analyzed to be 16.75% w HESA (14.56 g acid) or ~97.7% overall acid recovery in the overhead.

Example 10: Reversion of HESA Salts was Carried Out in a Pretreatment Recycle Stream that has Already been Stripped A liquid recycle stream was produced by the process described in US2013/0295629 where a slow build-up to steady state of the HESA salt of the acid was seen. Free acid is overheaded and recycled during the process. The HESA anion was shown to have a ratio of 0.019 to water in the stream on a weight basis. Further, the material heavier than water (sugars, salts, and other solubles) was found to be ~15% w by evaporation and gravimetric measurement. Therefore, the HESA anion in the total solution was ~1.6% w overall or about 16.0 g overall. The Ca2+ and K+ ions in solution (by x-ray fluorescence) were an approximate match on a mole basis with the HESA anion found in solution.

Into a 2 liter autoclave equipped with a DiComp IR probe was placed 1000.13 g of the liquid recycle stream at steady state from the pretreatment of corn stover containing ~1.6% w of the HESA anion from the ions present in the biomass. To this material 7.63 g of 96% w sulfuric acid was added. After the addition of the sulfuric acid was complete, the reactor was sealed. It was fitted with heating bands and the stirrer was started (1000 rpm). The system was then purged lightly three times with nitrogen prior to heating. The sample was then heated to 105° C. The reactor pressure was approximately 20 psig.

Upon reaching 105° C., the acid reversal was accomplished via opening the gas cap of the reactor to an overhead condensation system for recovery of the acid and holding the reactor temperature at approximately 100° C. This overhead system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with about 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of a hydroxyethane sulfonic acid or anion. The IR of the overheads revealed that the concentration of the HESA at this point had reached a maximum and then started to decrease due to dilution with condensed water, free of a hydroxyethane sulfonic acid component, building in the recovery flask. The reactor was then sealed and cooled to room temperature. The residual liquid in the Parr reactor and the overhead recovered acid was analyzed via proton NMR for HESA concentration.

A total of 196.22 g of material was captured in the overhead system for a total of 596.22 g (400 g DI water initially present). The proton NMR analysis showed 2.51% w HESA present or a total of approximately 15.0 g with an overall recovery of about 93% of the original HESA anion present as salts in the recycle stream.

Example 11: Example 10 was Repeated with the Addition of 8.64 g of 85% w Phosphoric Acid Instead of Sulfuric Acid A liquid recycle stream was produced by the process described in US2013/0295629 where a slow build-up to steady state of the HESA salt of the acid was seen. Free acid is overheaded and recycled during the process. The HESA anion was shown to have a ratio of 0.019 to water in the stream on a weight basis. Further, the material heavier than water (sugars, salts, and other solubles) was found to be ~15% w by evaporation and gravimetric measurement. Therefore, the HESA anion in the total solution was ~1.55% w or 15.5 g overall. The Ca2+ and K+ ions in solution (by x-ray fluorescence) were an approximate match on a mole basis with the HESA anion found in solution.

Into a 2 liter autoclave equipped with a DiComp IR probe was placed 1000.13 g of the liquid recycle stream at steady state from the pretreatment of corn stover containing ~1.55% w of the HESA anion or about 15.5 g in the recycle stream. To this material 8.64 g of 85% w phosphoric acid was added. After the addition of the sulfuric acid was complete, the reactor was sealed. It was fitted with heating bands and the stirrer was started (1000 rpm). The system was then purged lightly three times with nitrogen prior to heating. The sample was then heated to 105° C. The reactor pressure was approximately 20 psig.

Upon reaching 105° C., the acid reversal was accomplished via opening the gas cap of the reactor to an overhead condensation system for recovery of the acid and holding the reactor temperature at approximately 100° C. This overhead system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with about 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of the α hydroxyethane sulfonic acid or anion. The IR of the overheads revealed that the concentration of the HESA at this point had reached a maximum and then started to decrease due to dilution with condensed water, free of a hydroxyethane sulfonic acid components, building in the recovery flask. The reactor was then sealed and cooled to room temperature. The residual liquid in the Parr reactor and the overhead recovered acid was analyzed via proton NMR for HESA concentration.

A total of 223.14 g of material was captured in the overhead system for a total of 623.14 g (400 g DI water initially present). The proton NMR analysis showed 2.35% w HESA present or a total of approximately 14.6 g with an overall recovery of about 94% of the original HESA anion that was present as salts in the recycle stream.

We claim:
1. A method for recovering α-hydroxysulfonic acid in a biomass treatment process comprising:
   (a) providing a biomass containing polysaccharides;
   (b) contacting the biomass with a solution containing at least one α-hydroxysulfonic acid thereby hydrolyzing the biomass to produce a product stream containing at least one fermentable sugar, α-hydroxysulfonic acid, and at least one salt of α-hydroxysulfonic acid;
   (c) contacting at least a portion of the salt of α-hydroxysulfonic acid with a mineral acid forming α-hydroxysulfonic acid and a salt of the mineral acid;
   (d) separating at least a portion of the α-hydroxysulfonic acid from the mineral acid by heating and/or reducing pressure and recovering the α-hydroxysulfonic acid in its component form; and
   (e) recovering from the product stream an acid-removed product containing at least one fermentable sugar.

2. The method of claim 1 wherein the α-hydroxysulfonic acid is recovered by removing at least a portion of the α-hydroxysulfonic acid in its component form from the product by heating and/or reducing pressure to produce an acid-removed product containing at least one fermentable sugar.

3. The method of claim 1 wherein the mineral acid is present in an amount from 0.1 equivalent to 1.2 equivalent to the salt of α-hydroxysulfonic acids in step (c).

4. The method of claim 3 wherein the mineral acid is provided to step (c).

5. The method of claim 1 wherein the α-hydroxysulfonic acid is present in an amount of from about 1% wt. to about 55% wt., based on the solution.

6. The method of claim 1 wherein the α-hydroxysulfonic acid is produced from (a) a carbonyl compound or a precursor to a carbonyl compound with (b) sulfur dioxide or a precursor to sulfur dioxide and (c) water.

7. The method of claim 1 wherein the α-hydroxysulfonic acid is in-situ generated.

8. The method of claim 5 wherein step (b) is carried out at a temperature within the range of about 50° C. to about 150° C. and a pressure within the range of 0.5 bara to about 11 bara.

9. The method of claim 1 wherein the mineral acid is selected from the group consisting of sulfuric acid, phosphoric acid, hydrochloric acid, and mixtures thereof.

10. The method of claim 9 wherein step (b) is carried out at a temperature within the range of about 50° C. to about 150° C. and a pressure within the range of 0.5 bara to about 11 bara.

11. The method of claim 1 wherein step (c) is carried out at a temperature within the range from about 50° C. to about 150° C.

12. The method of claim 11 wherein step (d) is carried out at a temperature within the range from about 50° C. to about 150° C. and a pressure within the range from about 0.1 bara to about 5 bara.

13. The method of claim 12 wherein the mineral acid is selected from the group consisting of sulfuric acid, phosphoric acid, hydrochloric acid, and mixtures thereof.

14. The method of claim 13 wherein up to about an equivalent molar amount of mineral acid to the amount of the salt of α-hydroxysulfonic acid is provided to step (c).

15. The method of claim 1 wherein the mineral acid is provided to step (b).

16. The method of claim 1 wherein the at least one fermentable sugar comprises at least one pentose and/or at least one hexose.

17. The method of claim 1 further comprising separating a liquid stream containing said fermentable sugar and a wet solid stream containing remaining biomass from the acid-removed product.

18. The method of claim 17 wherein at least a portion of the liquid stream is recycled to step (b).

19. The method of claim 18 wherein the mineral acid is provided to the recycle of the liquid stream.

20. The method of claim 17 further comprising hydrolyzing the wet solid stream thereby producing a sugar stream.

21. The method of claim 20 further comprising fermenting the sugar stream thereby producing fermented products.

22. The method of claim 2 further comprising hydrolyzing and fermenting the stream containing fermentable sugar thereby producing fermented products.

23. The method of claim 1 wherein the recovered α-hydroxysulfonic acid is recycled to step (b) as components or in its recombined form.

24. The method of claim 9 wherein the recovered α-hydroxysulfonic acid is recycled to step (b) as components or in its recombined form.

25. The method of claim 13 wherein the recovered α-hydroxysulfonic acid as components is recycled to step (b) as components or in its recombined form.

26. The process of claim 13 wherein the biomass is contacted with the α-hydroxysulfonic acid at a temperature of 120° C. or less.

27. A method for recovering α-hydroxysulfonic acid in a biomass treatment process comprising:
 (a) providing a biomass containing polysaccharides;
 (b) contacting the biomass with a solution containing at least one α-hydroxysulfonic acid in an amount of from about 1% wt. to about 55% wt., based on the solution, at a temperature within the range of about 50° C. to about 150° C. and a pressure within the range of 0.5 bara to about 11 bara thereby hydrolyzing the biomass to produce a product stream containing at least one fermentable sugar, α-hydroxysulfonic acid, and at least one salt of α-hydroxysulfonic acid;
 (c) contacting at least a portion of the salt of α-hydroxysulfonic acid with a mineral acid in an amount from about 0.1 equivalent to about 1.2 equivalent amount of mineral acid to the salt of α-hydroxysulfonic acid, said mineral acid is selected from the group consisting of sulfuric acid, phosphoric acid, hydrochloric acid, and mixtures thereof, at a temperature within the range from about 50° C. to about 150° C. forming α-hydroxysulfonic acid and a salt of the mineral acid;
 (d) separating at least a portion of the α-hydroxysulfonic acid from the mineral acid at a temperature within the range from about 50° C. to about 150° C. and a pressure within the range from about 0.1 bara to about 5 bara with the proviso that (i) the temperature is higher than step (b), (ii) the pressure is less than step or (iii) the temperature is higher and pressure is lower than step (b), and recovering the α-hydroxysulfonic acid in its component form; and
 (e) recovering from the product stream an acid-removed product containing at least one fermentable sugar.

28. The method of claim 27 wherein the mineral acid is phosphoric acid.

29. The method of claim 27 wherein the mineral acid is sulfuric acid.

30. The method of claim 27 wherein the mineral acid is hydrochloric acid.

31. The method of claim 27 wherein the acid-removed product is further processed to produce at least one organic compound.

32. The method of claim 1 wherein the acid-removed product is further processed to produce at least one organic compound.

* * * * *